United States Patent [19]

Leitz et al.

[11] Patent Number: 5,153,291
[45] Date of Patent: Oct. 6, 1992

[54] TRIALKYLSILYLOXY-1,1-DIPHENYL ETHYLENES AND POLYMERS PRODUCED THEREWITH

[75] Inventors: Edgar Leitz, Dormagen; Hans-Josef Buysch; Ludwig Bottenbruch, both of Krefeld; Karl-Heinz Ott, Leverkusen, all of Fed. Rep. of Germany

[73] Assignee: Bayer Aktiengesellschaft, Leverkusen, Fed. Rep. of Germany

[21] Appl. No.: 492,843

[22] Filed: Mar. 13, 1990

Related U.S. Application Data

[62] Division of Ser. No. 367,002, Jun. 16, 1989, Pat. No. 4,956,485.

Foreign Application Priority Data

Jun. 28, 1988 [DE] Fed. Rep. of Germany ....... 3821745

[51] Int. Cl.$^5$ ............................................. C08F 30/08
[52] U.S. Cl. ................................. 526/279; 525/333.1; 525/333.2; 525/333.3; 525/342; 525/384; 556/446; 556/486
[58] Field of Search ................ 526/279; 556/446, 486; 525/333.1, 333.2, 333.3, 342, 384

[56] References Cited

U.S. PATENT DOCUMENTS 4,283,505  8/1981  Kleeberg et al. ................ 556/486

FOREIGN PATENT DOCUMENTS 1235894  3/1967  Fed. Rep. of Germany .

*Primary Examiner*—Paul R. Michl
*Assistant Examiner*—Edward J. Cain
*Attorney, Agent, or Firm*—Connolly and Hutz

[57] ABSTRACT

Trialkylsilyloxy-1,1-diphenyl ethylenes corresponding to general formula I, new polymers produced therewith terminated by aryl trialkylsilyl ether groups or by phenolic hydroxyl groups and a process for the production of these polymers by anionic polymerization

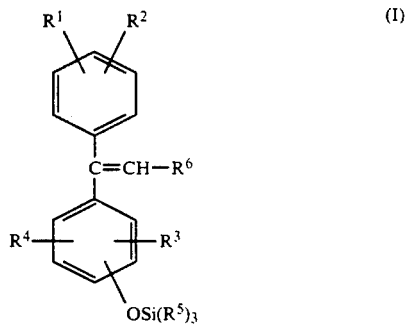

in which
$R^1$, $R^2$=H, $C_1$-$C_4$ alkyl, $OCH_3$,
$R^3$=H, $C_1$-$C_4$ alkyl, O—$C_1$-$C_4$ alkyl,
$R^4$=H, $C_1$-$C_4$ alkyl,
$R^5$=$C_1$-$C_4$ alkyl,
$R^6$=H, $C_1$-$C_4$ alkyl.

6 Claims, No Drawings

TRIALKYLSILYLOXY-1,1-DIPHENYL ETHYLENES AND POLYMERS PRODUCED THEREWITH

This application is a division of application Ser. No. 367,002, filed on Jun. 16, 1989, now U.S. Pat. No. 4,956,485.

This invention relates to trialkylsilyloxy1,1-diphenyl ethylenes corresponding to general formula I and to new polymers produced therewith terminated by aryl trialkylsilyl ether groups or by phenolic hydroxyl groups and to a process for the production of these polymers by anionic polymerization.

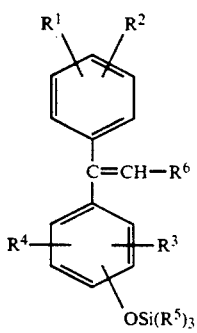

in which
$R^1$, $R^2$=H, $C_1$-$C_4$ alkyl, $OCH_3$,
$R^3$=H, $C_1$-$C_4$ alkyl, O—$C_1$—$C_4$ alkyl,
$R^4$=H, $C_1$-$C_4$ alkyl,
$R^5$=$C_1$-$C_4$ alkyl
$R^6$=$C_1$-$C_4$ alkyl.

German Offenlegungsschrift 37 25 848 describes the production of polymeric dihydroxy compounds by anionic polymerization of suitable compounds, reduction of the reactivity of the polyanion by 1,1-diphenyl ethylene in an optional step, reaction with 2,5-dimethoxy benzyl bromide and removal of the protective group by subsequent ether cleavage with trimethyl iodosilane, trimethyl chlorosilane or sodium iodide or acids.

The compounds are suitable as stabilizers for polymers, particularly those containing unsaturated bonds in the polymer chain, against thermal, radiation-induced and oxidative degradation.

The reaction of so-called "living" polymers (such as polystyryl lithium) with halogen compounds containing other functional groups gives functional polymers, but is accompanied by a number of secondary reactions (cf. J. Polym. Sci. A 3, 4131 (1965; Polymer 17, 1020 (1976); J. Polym. Sci. B 14, 471 1976; Adv. polym. Sci. 56, 72 (1984)). The yield of functional polymer is often not satisfactory. Accordingly, this reaction is not suitable for large scale manufacture.

The present invention relates to trialkylsilyloxy-1,1-diphenyl ethylenes corresponding to formula (I), to polymers produced therefrom terminated by aryl trialkylsilyl ether groups or by phenolic hydroxyl groups corresponding to formulae (II) and (III) and to corresponding production processes.

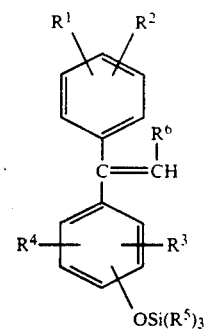

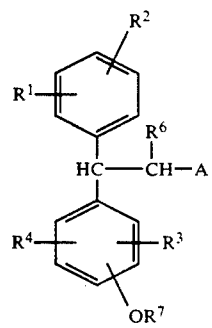

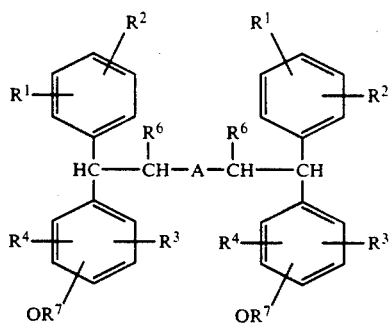

in which
A=a polymer of anionically polymerizable vinyl compounds,
$R^1$, $R^2$=H, $C_1$-$C_4$ alkyl, $OCH_3$
$R^3$=H, $C_1$-$C_4$ alkyl, O—$C_1$—$C_4$ alkyl,
$R^4$=H, $C_1$-$C_4$ alkyl,
$R^5$=$C_1$-$C_4$ alkyl,
$R^6$=H, $C_1$-$C_4$ alkyl
$R^7$=H, $Si(R^5)_3$.

The trialkylsilyloxy diphenyl ethylenes of formula (I) according to the invention may be obtained by methods known per Hydroxy diphenyl ethylenes corresponding to formula (V) may be obtained by the alkali-catalyzed thermal cleavage of 1-alkyl-1-phenyl-bis-(hydroxyphenyl)-methane corresponding to formula (IV) (DE-AS 1 235 894):

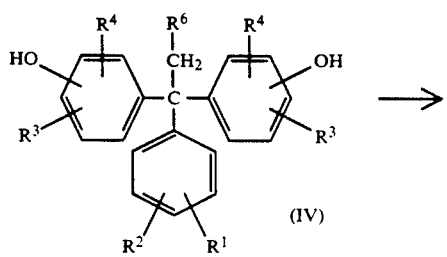

-continued

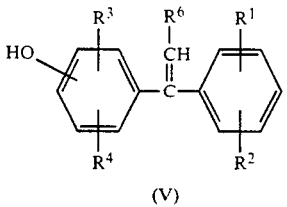

(V)

In formulae IV and V, $R^1$, $R^2$, $R^3$, $R^4$ and $R^5$ are as defined above.

The trialkylsilyloxy-1,1-diphenyl ethylenes I) are formed by reaction of the hydroxy diphenyl ethylenes corresponding to formula (V) with halosilanes corresponding to formula (VI) in the presence of acid acceptors (I).

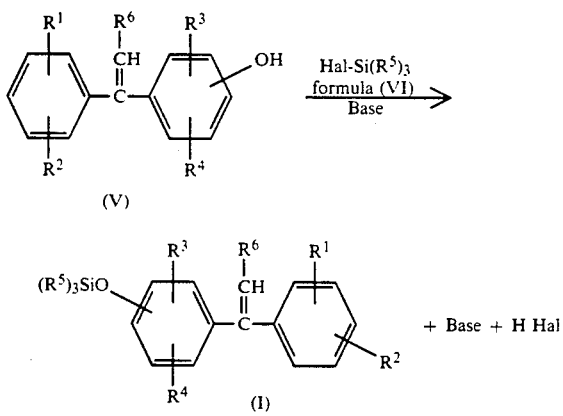

Hal=Cl, Br.

Accordingly, the starting products for the production of the compounds of formula (I) according to the invention are 1-alkyl-1-phenyl-bis-(hydroxyphenyl)-methanes corresponding to formula (IV), in which the substituents $R^1$ to $R^6$ are as defined above.

The following are examples of compounds corresponding to formula (IV):
1-methyl-1-phenyl-bis-(4-hydroxyphenyl)-methane
1-ethyl-1-phenyl-bis-(4-hydroxyphenyl)-methane,
1-propyl-1-phenyl-bis-(4-hydroxyphenyl)-methane,
1-pentyl-1-phenyl-bis-(4-hydroxyphenyl)-methane,
1-methyl-1-(4-methylphenyl)-bis-(4-hydroxyphenyl)-methane,
1-methyl-1-(4-methoxyphenyl)-bis-(4-hydroxyphenyl)-methane,
1-methyl-1-(3,5-dimethylphenyl)-bis-(4-hydroxyphenyl)methane,
1-methyl-1-phenyl-bis-(2-hydroxyphenyl)-methane,
1-methyl-1-phenyl-[(4-hydroxyphenyl)-(2,-hydroxyphenyl)]methane,
1-methyl-1-phenyl-bis-(3-methyl-4-hydroxyphenyl)-methane,
1-methyl-1-phenyl-bis-(3-methoxy-4-hydroxyphenyl)-methane,
1-1-phenyl-bis-(3,5-dimethyl-4-hydroxyphenyl)methane,
1-methyl-1-phenyl-bis-(3,5-dimethyl-2-hydroxyphenyl)methane.

Preferred compounds corresponding to formula (IV) are those containing the following substituents:
$R^1$=H,
$R^2$=H, $CH_3$, $OCH_3$,
$R^3$=H, $CH_3$, $OCH_3$,
$R^4$=H, $CH_3$,
R=H, $CH_3$, More preferably, $R^1$, $R^2$, $R^3$, $R^4$ and $R^5$ are hydrogen.

The compounds corresponding to formula (IV) may be cleaved under the conditions described in DE-AS 1 235 894. Suitable halosilanes for the reaction of the compounds corresponding to formula (V) to the trialkylsilyloxy diphenyl ethylenes of formula (I) according to the invention correspond to formula (VI).

Examples of halosilanes corresponding to formula (VI) are trimethyl chlorosilane, triethyl bromosilane, tripropyl chlorosilane, diethyl methyl chlorosilane. Trimethyl chlorosilane and triethyl chlorosilane are preferred, trimethyl chlorosilane being particularly preferred.

Compounds corresponding to formula (V) may generally be reacted with those of formula (VI) in a molar ratio of 1:1 (or with a slight excess of (VI)) in inert solvents, such as hydrocarbons (gasoline, ligroin, heptane, pentane, cyclohexane, benzene, toluene, xylene), halogenated hydrocarbons (chloroform, methylene chloride, dichloroethane, chlorobenzene) or ethers (diethyl ether, diisopropyl ether, dibutyl ether); the reaction is preferably carried out in hydrocarbons in the presence of a base, such as ammonia, triethyl amine, tributyl amine, pyridine, N-methyl imidazole, quinoline. However, the compound of formula (V) may also be converted into a salt and the salt reacted in dry form with the halosilane. Apart from the amine salts mentioned above, suitable salts are also salts of lithium, sodium and potassium.

The reaction temperature is in the range from 0° to 120° C. and preferably in the range from 10° to 100° C.

The base must be used in an at least stoichiometric quantity based on (V), best in a slight excess.

After separation of the salts formed during the reaction, for example by filtration, the compounds corresponding to formula (I) may be directly used as such, although additional purification by distillation is possible.

The following are examples of suitable compounds of formula (I) for the production of the new polymers:
4-methyl-4'-trimethylsilyloxy-1,1-dipenyl ethylene,
4-ethyl-4'-triethylsilyloxy-1,1-diphenyl ethylene,
3-methoxy-4'-trimethylsilyloxy1,1-diphenyl ethylene,
4-isopropyl-4'-triethylsilyloxy-1,1-diphenyl ethylane,
4-methyl-2'-trimethylsilyloxy-5'-methyl 1,1-diphenyl ethylene,
3-methyl-4-trimethylsilyloxy-1,1-diphenyl ethylene,
4-methoxy-2'-trimethylsilyloxy-3',5'-dimethyl 1,1-diphenyl ethylene,
3-methoxy-4-trimethylsilyloxy-1,1-diphenyl ethylene,
4-trimethylsilyloxy-β-methyl1,1-diphenyl ethylene,
4-trimethylsilyloxy-β-propyl-1,1-diphenyl ethylene,
4-Trimethylsilyloxy-1,1diphenyl ethylene is particularly preferred.

The process according to the invention for the production of the polymeric compounds terminated by aryl trimethylsilyl ether groups or of the polymeric compounds terminated by phenolic hydroxyl groups corresponding to formulae (II) and (III) involves the following steps:
1. Preparation of a polyanion by anionic polymerization of a suitable vinyl compound.
2. Reaction of the polyanion with a compound corresponding to formula (I)

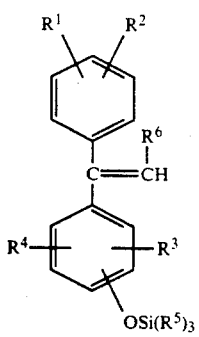

(I)

in which $R^1$ to $R^5$ are as defined above.

3. Neutralization of the reaction products (which are themselves polyanions) with protic compounds to form the polymeric compounds terminated by aryl trisilyloxy ether groups corresponding to formulae (II) and (III) in which $R^7=Si(R^5)_3$.
4. Optionally, silyl ether cleavage for the production of the polymeric compounds terminated by phenolic hydroxyl groups corresponding to formulae (II) and (III) in which $R^7=H$.

In step 1, anionically polymerizable vinyl compounds are polymerized in aromatic or aliphatic hydrocarbons or an ether with an alkyl alkali metal compound, aryl alkali metal compound or an oligomeric o-methyl styrene/alkali metal compound with formation of a "living" polyanion or polydianion, the reaction being continued to complete conversion of the monomer. In step 2, the polyanion or polydianion is reacted with compounds corresponding to formula (I), resulting in the formation of a new polyanion or polydianion. In step 3, the polyanion or polydianion is neutralized with protic compounds and the polymer (II) or (III) terminated by aryl trisilyloxy ether groups ($R^7=Si(R^5)_3$) is isolated.

To produce the polymers (II) or (III) terminated by phenolic hydroxyl groups ($R^7=H$), the polyanion or dianion is neutralized after steps 1 and 2 in step 3, the product is optionally isolated and the silyl ether is cleaved.

Suitable anionically polymerizable compounds in the context of the invention are e.g. styrene, p-methyl styrene, vinyl pyridine, vinyl naphthalene, isopropenyl naphthalene, 1,3-butadiene, isoprene or mixtures thereof. Preferred are styrene, 1,3-butadiene, isoprene or mixtures of styrene/1,3-butadiene and styrene/isoprene. and styrene/isoprene.

Suitable aromatic and aliphatic hydrocarbons in the context of the invention are e.g. toluene, benzene, xylene, pentane, hexane, cyclohexane. Ethers in the context of the invention are e.g. tetrahydrofuran and dioxane. A mixture of aromatic or aliphatic hydrocarbons and ethers may also be used to adjust certain reaction velocities.

To prepare the polymers corresponding to formula (II), alkyl alkali metal compounds, particularly n-butyl lithium or sec.-butyl lithium, are preferably used as initiators.

To prepare the polymer corresponding lo formula III, aryl alkali metal compounds, particularly naphthalene sodium, naphthalene potassium, oligo-α-methyl styryl odium, oligo-α-methyl styryl potassium or 1,3 -Phanylen-bis(3-methyl-1-phenyl-pentyliden)-bis(lithium), are preferably used as initiators The anionically polymerizable compounds may be polymerized at $-100°$ C. to $+80°$ C. and preferably at $-78°$ C. to 50° C.

The "living" polymer anions may be reacted with the compound (I) at $-78°$ C. to $+100°$ C and preferably at 0° C. to $+50°$ C. Compound (I) is preferably used in excess, based on initiator.

Suitable neutralizing agents for the "living" polymer anions are, for example, weak inorganic or organic acids, particularly methanol or acetic acid.

Since the process according to the invention uses "living" carbanions, it is of course necessary to maintain conditions under which "living" carbanions are stable, for example an inert atmosphere, absence of atmospheric oxygen and moisture.

The silyl ethers corresponding to formulae (II) and (III) ($R^7=Si(R^5)_3$) may advantageously be cleaved by acidification of their solutions with inorganic acids (for example hydrochloric acid) or organic acids (for example p-toluene sulfonic acid). The cleavage is carried out at temperatures in the range from room temperature to the boiling temperature of the solvent.

The polymers of formulae (II) and (III) ($R^7=H$) according to the invention may be isolated by precipitation of the polymer from the solution, preferably using methanol, or by evaporation of the polymer solution in known evaporation units.

The polymers of formulae (II) and (III) according to the invention have molecular weights (controllable through the ratio of monomer concentration to initiator concentration) of from 500 g/mol to 500,000 g/mol, preferably from 1000 g/mol to 250,000 g/mol and more preferably from 1000 g/mol to 100,000 g/mol.

The polymers of formulae (II) and (III) according to the invention are suitable as stabilizers and/or lubricants for synthetic polymers and ($R^7=H$) for the build-up of polycondensates.

EXAMPLES

1.1 Preparation of 1-methyl-1-phenyl-bis-(4-hydroxyphenyl)-methane:

A mixture of 240 g (2 mol) acetophenone, 940 g (10 mol) phenol and 30 g mercapto propionic acid is saturated with HCl gas and, at the same time, is slowly heated to 50° C. The mixture is then kept under these conditions for 5 hours and left standing overnight, after which first HCl and water are distilled off in a water jet vacuum, followed by the excess phenol up to a sump temperature of 120° C. The residue of 510 g is dissolved in and reprecipitated under reflux from 1250 ml toluene, filtered under suction after cooling and dried: 412 g, Mp. 185°–7° C., i.e. 72% of the theoretical (MW 580).

1.2 Preparation of 4-hydroxyl,1-diphenyl ethylene:

400 g of the triphenyl methane derivative obtained as described above are heated with 4 g NaOH to 180°–220° C. The cleavage products distill over at 130°–160° C. and approx. 15 mbar. A total of 340 g distillate and approx. 56 g of a brown resin-like residue are obtained.

A fraction of 120 g corresponding to the title compound is isolated from this distillate by redistillation (45% of the theoretical; MW 196).

1.3 Preparation of 4-trimethylsilyloxy1,1-diphenyl ethylene:

100 g (0.51 mol) of the 4-hydroxy1,1diphenyl ethylene obtained by cleavage are dissolved in 200 ml cyclohexane, 56 g (0.56 mol) triethyl amine are added to the resulting solution and 56 g (0.56 mol) trimethyl chlorosilane are added dropwise thereto over a period of about 1 h at room temperature to 50° C. After another 2 h at 50° C., the salt precipitated is filtered off under pressure, the filter cake is thoroughly washed with cyclohexane and the entire filtrate is distilled. Redistillation of the main fraction, $Bp_{1.5} 143°-8°$ C., gives 11? g of a colorless liquid ($n_D^{20}=1.5558$) which, according to NMR, corresponds to the title compound and is at least 95% pure (67% of the theoretical).

1.4 Reaction of a "living" polystyrene anion with 4-trimethylsilyloxy diphenyl ethylene (preparation of the polymer of formula (II) with $R^7=Si(R^5)$):

6.5 ml of a 2.5 molar n-butyl lithium solution (in hexane) were introduced by syringe with rapid stirring at room temperature in a nitrogen atmosphere into a mixture of 800 ml toluene and 100.2 g styrene, the solution turning orange-red in color. The temperature was then increased to 40° C. After a polymerization time of 3 h, the solution was brought to room temperature and 45 ml of a solution of 10 g 4-trimethylsilyloxy-1,1diphenyl ethylene and 60 g toluene were added by means of a syringe, the solution turning dark red in color. The reaction time was 1 h at room temperature. The polymer was then neutralized with 2 ml methanol (nitrogen-saturated) and isolated by precipitation in methanol.

1.5 Cleavage of the silyl ether (preparation of a polymer of formula (II) ($R^7=H$)):

20 ml of a 10% aqueous hydrochloric acid were added at 40° C. to a solution of 100 g of the polymer described in the above Example in 800 ml tetrahydrofuran. The reaction time Was 1 h. The polymer was then precipitated in methanol, washed until neutral and dried.
GPC analysis (calibration: polystyrene):
$M_n=6\,500$ g/mol,
$M_w=7\,900$ g/mol.

2.1 Reaction of a "living" polystyrene dianion with 4-trimethylsilyloxy-1,1diphenyl ethylene preparation of the polymer of formula (III) with $R^7=Si(R^5)_3$):

4 g (0.031 mol) naphthalene are added under nitrogen to 0.55 g (0.024 mol) sodium in 250 ml tetrahydrofuran, the solution turning bright green in color. After about 2 h at room temperature, the sodium had completely reacted to naphthalene sodium. 50 g styrene were then added dropwise by syringe over a period of 2 h, the color turning to red. After another 30 minutes, a solution of 8 g (0.03 mol) 4-trimethyl silyloxy-1,1-diphenyl ethylene and 15 ml toluene was added by syringe. After a reaction time of 2 h at room temperature, the polymer was neutralized with methanol (nitrogen-saturated) and isolated by precipitation in methanol.

2.2 Cleavage of the silyl ether (preparation of the polymer of formula (III) with $R^7=H$)):

35 ml of 10% aqueous hydrochloric acid were added at 40° C. to a solution of 45 g of the polymer described in the above Example in 350 ml tetrahydrofuran. After a reaction time of 1 hour, the polymer was precipitated in methanol, isolated, washed until neutral and dried.

We claim:
1. Polymeric compounds terminated by aryl trialkylsilyl ether groups corresponding to formula (I)

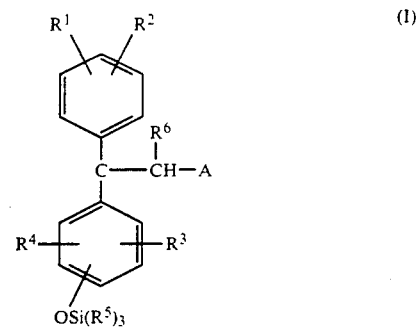

or by phenolic hydroxyl groups corresponding to formula (II) and (III)

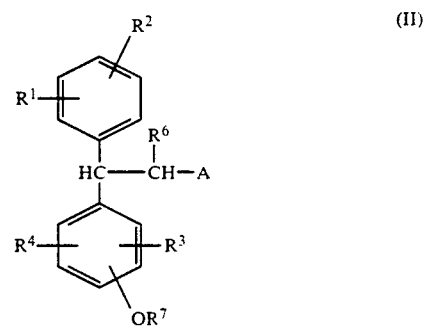

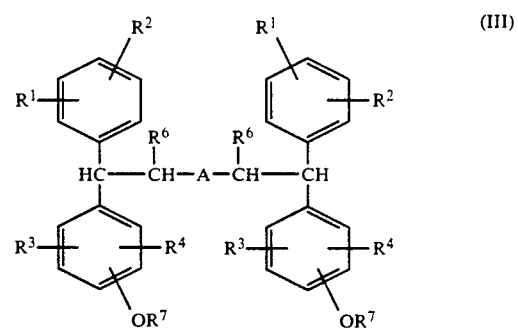

in which
A is a polymer of anionically polymerizable vinyl compounds and
$R^1$, $R^2$=H, $C_1$-$C_4$ alkyl, $OCH_3$,
$R^3$=H, $C_1$-$C_4$ alkyl, O—$C_1$-$C_4$ alkyl,
$R^4$=H, $C_1$-$C_4$ alkyl,
$R^5$=$C_1$-$C_4$alkyl,
$R^6$=H, $C_1$-$C_4$alkyl
and $R^7$ is hydrogen or —$Si(R^5)_3$.

2. Polymeric compounds terminated by aryl trialkylsilyl ether groups and by phenolic hydroxyl groups as claimed in claim 1, in which A is a polymer synthesized from styrene, p-methyl styrene, vinyl naphthalene, isopropenyl naphthalene, vinyl pyridine, 1,3-butadiene, isoprene or mixtures thereof.

3. A process for the production of the polymeric compounds terminated by aryl trialkylsilyl ether groups claimed in claim 1, characterized in that
   1. monomers are anionically polymerized,
   2. the "living" polymer anions formed in step 1 are reacted with a compound corresponding to formula (I),
   3. the polymer anions formed in step 2 are neutralized and the polymer is isolated.

4. A process for the production of the polymeric compounds terminated by phenolic hydroxyl groups claimed in claim 1, characterized in that
1. monomers are an ionically polymerized,
2. the "living" polymer anions formed in step are reacted with a compound corresponding to formula (I),
3. the polymer anions formed in step 2 are neutralized, the polymer is optionally isolated and the silyl ether is cleaved.

5. Polymeric compounds terminated by aryl trialkylsilyl ether groups on by phenolic hydroxyl groups as claimed in claim 1, in which
$R^1$ is H;
$R^2$ is H or $CH_3$ or $PCH_3$;
$R^4$ is H or $CH_3$;
$R^5$ is $C_1$–$C_4$ alkyl; and
$R^6$ is H or $CH_3$.

6. Polymeric compounds terminated by aryl trialkylsilyl ether groups as claimed in claim 1, in which each of $R^1$, $R^2$, $R^3$, $R^4$ and $R^6$ are hydrogen and $R^5$ is methyl.

* * * * *